United States Patent
Wang et al.

(10) Patent No.: US 11,111,234 B2
(45) Date of Patent: Sep. 7, 2021

(54) SALT OF A QUINAZOLINE DERIVATIVE-LIKE TYROSINE KINASE INHIBITOR AND CRYSTAL FORM THEREOF

(71) Applicant: Xuanzhu Pharma Co., Ltd., Jinan (CN)

(72) Inventors: Jinyuan Wang, Jinan (CN); Zhenhua Wang, Jinan (CN); Yuzhen Feng, Jinan (CN)

(73) Assignee: XUANZHU PHARMA CO., LTD., Jinan (CN)

( * ) Notice: Subject to any disclaimer, the term of this patent is extended or adjusted under 35 U.S.C. 154(b) by 195 days.

(21) Appl. No.: 16/325,051

(22) PCT Filed: Aug. 11, 2017

(86) PCT No.: PCT/CN2017/097078
§ 371 (c)(1),
(2) Date: Feb. 12, 2019

(87) PCT Pub. No.: WO2018/028673
PCT Pub. Date: Feb. 15, 2018

(65) Prior Publication Data
US 2021/0053944 A1    Feb. 25, 2021

(30) Foreign Application Priority Data
Aug. 12, 2016 (CN) .......................... 201610663470.5

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC ............................ C07D 403/12; A61K 31/517
USPC ...................................... 544/293; 514/210.21
See application file for complete search history.

(56) References Cited

U.S. PATENT DOCUMENTS

2013/0184297 A1  7/2013  Huang et al.
2014/0161801 A1  6/2014  Wu et al.

FOREIGN PATENT DOCUMENTS

| CN | 101918390 A | 12/2010 |
| CN | 103347876 B | 10/2014 |
| WO | 2009/052264 A2 | 4/2009 |
| WO | 2012159457 A1 | 11/2012 |

OTHER PUBLICATIONS

International Search Report and Written Opinion dated Sep. 28, 2017, issued in International Application No. PCT/CN2017/097078, filed Aug. 11, 2017, 13 pages.

*Primary Examiner* — Jeffrey H Murray
(74) *Attorney, Agent, or Firm* — Christensen O'Connor Johnson Kindness PLLC

(57) ABSTRACT

Provided are a maleate of a quinazoline derivative-like tyrosine kinase inhibitor represented by Formula (1), and a crystal form thereof and a preparation method therefor, a pharmaceutical composition comprising the maleate and the crystal form thereof, as well as use of the maleate and the crystal form thereof in the manufacture of a medicament for treating and/or preventing a hyperproliferative disease and a chronic obstructive pulmonary disease.

15 Claims, 3 Drawing Sheets

SALT OF A QUINAZOLINE DERIVATIVE-LIKE TYROSINE KINASE INHIBITOR AND CRYSTAL FORM THEREOF

TECHNICAL FIELD

The present invention relates to a maleate of a quinazoline derivative-like tyrosine kinase inhibitor, a crystal form thereof and a preparation method therefor, a pharmaceutical composition, and use thereof in the manufacture of a medicament for treating and/or preventing a hyperproliferative disease and a chronic obstructive pulmonary disease.

BACKGROUND ART

The compound represented by Formula (1), (E)-N-(4-((3-chloro-4-fluorophenyl)amino)-7-methoxylquinazolin-6-yl)-4-(2-azaspiro[3.3]heptan-2-yl)-2-butenamide (abbreviated hereafter as "the compound of Formula (1)", which has been described in the patent application PCT/CN2012/000737), is a quinazoline derivative-like irreversible Pan-HER tyrosine kinase inhibitor. Studies have shown that irreversible Pan-HER tyrosine kinase inhibitors can effectively inhibit EGFR, and also have an inhibitory effect on HER2/4. Such drugs, which have an irreversible inhibitory effect on HER/ErbB family, can not only enhance the activity of drugs, but also reduce the generation of drug resistance, have a significantly inhibitory effect on Erlotinib-resistant H1975 cell line, and exert good anti-tumor activity.

Formula (1)

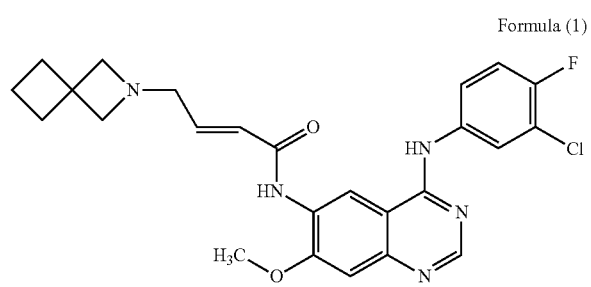 [SMILES: COc1cc2ncnc(Nc3ccc(F)c(Cl)c3)c2cc1NC(=O)/C=C/CN1CC2(CCC2)C1]

Research on crystal forms plays a very important role in drug development. Different crystal forms of the same drug are different from each other remarkably in terms of solubility, stability, bioavailability and the like. The patent application PCT/CN2012/000737 discloses a method for preparing a hydrochloride of the compound of Formula (1), however, during the preparation of a formulation, the hydrochloride has the shortcomings such as corrosion of instruments and equipment.

Contents of Invention

For better control of the quality of drugs to meet the demands in formulation, production, transportation and the like, the inventors conducted studies to the other salts and crystal forms of the compound of Formula (1), thereby obtaining the present invention.

The present invention relates to a maleate of a Pan-HER tyrosine kinase inhibitor represented by Formula (1), (E)-N-(4-((3-chloro-4-fluorophenyl)amino)-7-methoxylquinazolin-6-yl)-4-(2-azaspiro[3.3]heptan-2-yl)-2-butenamide, and Crystal form A thereof. The present invention also relates to a method for preparing the crystal form, a pharmaceutical composition comprising the maleate or the Crystal form A thereof, a method for preventing and/or treating a hyperproliferative disease and a chronic obstructive pulmonary disease by administering the maleate or the Crystal form A thereof, and use of the maleate or the Crystal form A thereof in the manufacture of a medicament for treating a hyperproliferative disease and a chronic obstructive pulmonary disease.

In particular, the present invention provides:

(1) A maleate of the compound of Formula (1), wherein the molar ratio of the compound of Formula (1) to maleic acid is 1:1-1:3, preferably 1:2-1:3, more preferably 1:2.

Formula (1)

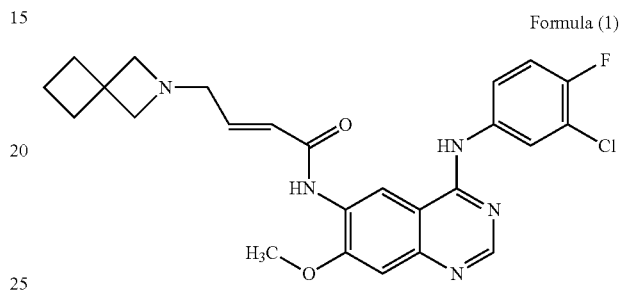

(2) Crystal form A of the maleate of the compound of Formula (1) according to Item (1), wherein, the X-ray powder diffraction pattern of which has characteristic peaks at the 2θ positions of 5.2±0.2°, 10.3±0.2°, 11.3±0.2°, 13.8±0.2°, 16.2±0.2°, and 19.9±0.2°, as determined by using Cu-Kα radiation.

(3) The Crystal form A of the maleate of the compound of Formula (1) as described above, wherein, the X-ray powder diffraction pattern of which further has characteristic peaks at the 2θ positions of 5.7±0.2°, 9.2±0.2°, 15.4±0.2°, and 18.7±0.2°, as determined by using Cu-Kα radiation.

(4) The Crystal form A of the maleate of the compound of Formula (1) according to Item (2) or (3), wherein, the X-ray powder diffraction pattern of which further has characteristic peaks at the 2θ positions of 18.4±0.2°, 20.6±0.2°, 21.2±0.2°, 22.7±0.2°, and 23.6±0.2°, as determined by using Cu-Kα radiation.

(5) The Crystal form A of the maleate of the compound of Formula (1) according to any one of Items (2) to (4), wherein, the X-ray powder diffraction pattern of which further has characteristic peaks at the 2θ positions of 7.2±0.2°, and 24.6±0.2°, as determined by using Cu-Kα radiation.

(6) The Crystal form A of the maleate of the compound of Formula (1) according to any one of Items (2) to (5), wherein, the X-ray powder diffraction pattern of which is substantially as shown in FIG. 1.

(7) The Crystal form A of the maleate of the compound of Formula (1) according to any one of Items (2) to (6), wherein, the DSC thermogram of which has an endothermic peak in the range from about 160° C. to 190° C., preferably from 170° C. to 185° C., and more preferably, the DSC thermogram of which is substantially as shown in FIG. 2.

(8) The Crystal form A of the maleate of the compound of Formula (1) according to any one of Items (2) to (7), which has a weight loss of about 5%-15% in the range from 150° C. to 250° C., and preferably has a TGA thermogram substantially as shown in FIG. 3.

(9) The Crystal form A of the maleate of the compound of Formula (1) according to any one of Items (2) to (8), which has a $^1$H NMR spectrum substantially as shown in FIG. 4.

(10) The Crystal form A of the maleate of the compound of Formula (1) according to any one of Items (2) to (9), the crystal structure of which is a substantially pure form.

(11) A method for preparing the Crystal form A of the maleate of the compound of the Formula (1), comprising reacting maleic acid with the compound of Formula (1) in a single solvent or a mixed solvent under heating, then cooling to precipitate crystal, followed by separating and drying to obtain the Crystal form A.

(12) The method according to Item (11), further comprising recrystallizing the Crystal form A of the maleate of the compound of Formula (1) in a single solvent or a mixed solvent.

(13) A pharmaceutical composition, comprising the maleate of the compound of Formula (1) according to Item (1) or the Crystal form A of the maleate of the compound of Formula (1) according to any one of Items (2) to (10), and one or more pharmaceutically acceptable carriers and/or diluents.

(14) The pharmaceutical composition according to Item (13), further comprising one or more second therapeutic agents selected from an antitumor agent and/or an immunosuppressor.

(15) A method for treating and/or preventing a hyperproliferative disease and a chronic obstructive pulmonary disease, comprising administering to a patient in need of such a therapy an effective amount of the maleate of the compound of Formula (1) according to Item (1) or the Crystal form A of the maleate of the compound of Formula (1) according to any one of Items (2) to (10).

(16) The method according to Item (15), comprising administering the maleate of the compound of Formula (1) or the Crystal form A of the maleate of the compound of Formula (1) according to any one of Items (2) to (10), in combined with one or more second therapeutic agents selected from the antitumor agent and/or the immunosuppressor.

(17) Use of the maleate of the compound of Formula (1) according to Item (1) or the Crystal form A of the maleate of the compound of Formula (1) according to any one of Items (2) to (10), or a combination thereof with the second therapeutic agent selected from antitumor agents and/or immunosuppressors, in the manufacture of a medicament for treating and/or preventing a hyperproliferative disease and a chronic obstructive pulmonary disease.

SPECIFIC MODES FOR CARRYING OUT THE INVENTION

Figure 1:
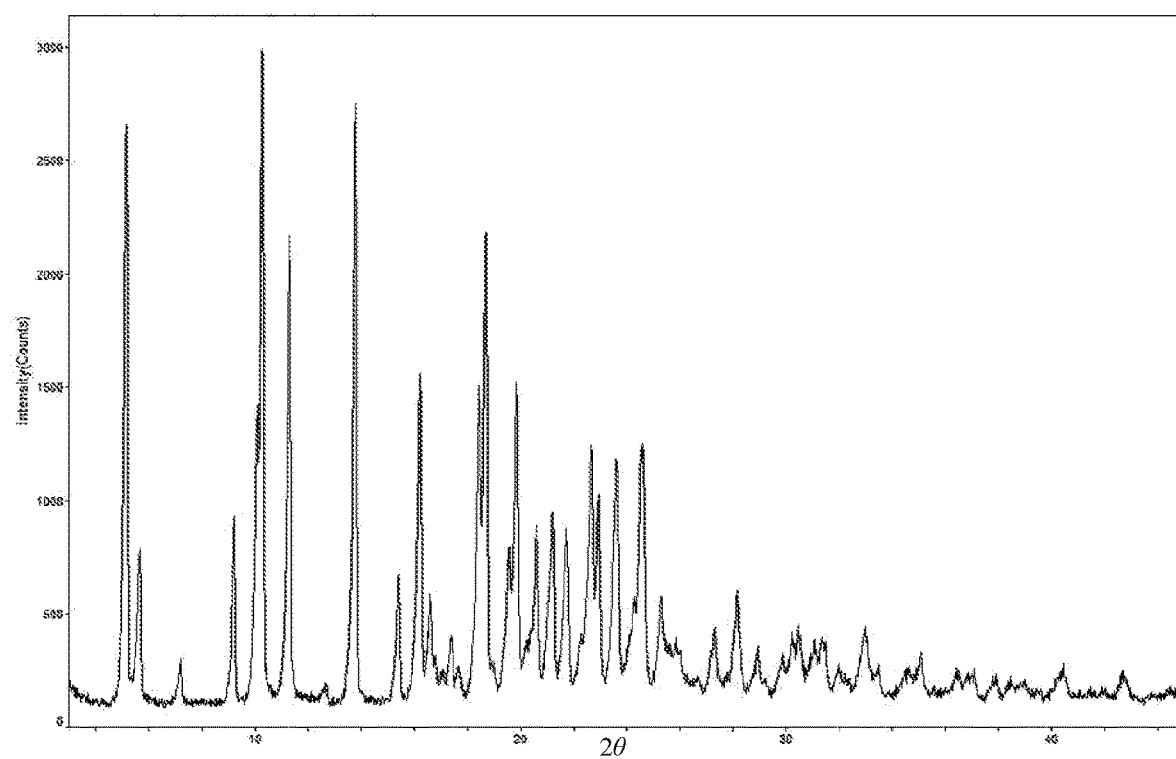
FIG. 1 shows the X-ray powder diffraction (XRPD) pattern of the Crystal form A of the maleate of the compound of Formula (1), wherein the ordinate represents diffraction intensity, and the abscissa represents the diffraction angle (2θ).

In the present application, the term "a single solvent" means that the solvent comprises only one component, including, but not limited to an alcohol, a nitrile, a ketone, an ester, an oxygen-containing heterocycle, a halogenated hydrocarbon and an aromatic hydrocarbon. Among them, the alcohol is preferably a lower alcohol, more preferably ethanol, propanol, isopropanol, n-butanol, isobutanol, tert-butanol, further preferably ethanol, isopropanol; the nitrile is preferably acetonitrile, propionitrile, more preferably acetonitrile; the ketone is preferably acetone, butanone, pentanone, methyl butyl ketone, methyl isobutyl ketone; the ester is preferably an aliphatic ester, more preferably methyl formate, ethyl formate, propyl formate, isopropyl formate, methyl acetate, ethyl acetate, propyl acetate, isopropyl acetate, methyl propionate, ethyl propionate, propyl propionate, isopropyl propionate, butyl acetate, isobutyl acetate, further preferably ethyl acetate, isopropyl acetate; the oxygen-containing heterocycle is preferably tetrahydrofuran, dihydropyran, tetrahydropyridine, 1,4-dioxane, more preferably tetrahydrofuran, 1,4-dioxane; the halogenated hydrocarbon is preferably 1,2-dichloroethane, 1,1-dichloroethane, chloroform; the aromatic hydrocarbon is preferably toluene, xylene.

The term "a mixed solvent" refers to a solvent consisting of two or more solvents at a certain ratio by volume, including, but not limited to the following mixed solvent systems: an alcohol/water, an ketone/water, a nitrile/water, an oxygen-containing heterocycle/water, an aprotic polar solvent/water, an aliphatic ether/aprotic polar solvent, a halogenated hydrocarbon/an aprotic polar solvent, an alcohol/ester, an ester/an aliphatic ether, and an ester/a halogenated hydrocarbon, wherein the aprotic polar solvent is selected from the group consisting of dimethyl sulfoxide, N-methylpyrrolidone, N,N-dimethylformamide, and 1,3-dimethyl-2-imidazolidinone; the aliphatic ether is selected from methyl tert-butyl ether; the oxygen-containing heterocycle is selected from 1,4-dioxane; the alcohol, ketone, nitrile, ester, and halogenated hydrocarbon are as described above; preferably an alcohol/water, a ketone/water, a nitrile/water, an oxygen-containing heterocycle/water, an aprotic polar solvent/water, an aliphatic ether/an aprotic polar solvent, a halogenated hydrocarbon/an aprotic polar solvent, further preferably ethanol/water, isopropanol/water, acetone/water, acetonitrile/water, 1,4-dioxane/water, dimethyl sulfoxide/water, N-methylpyrrolidone/water, N,N-dimethylformamide/water, methyl tert-butyl ether/N,N-dimethylformamide, methyl tert-butyl ether/N-methylpyrrolidone, chloroform/dimethyl sulfoxide, chloroform/N,N-dimethylformamide, or chloroform/N-methylpyrrolidone, and the certain volume ratio is 1:50-50:1, preferably 1:30-30:1.

Preferably, the method for preparing the Crystal form A of the maleate of the compound of Formula (1) comprising: adding maleic acid to the single solvent or the mixed solvent, and heating to a certain temperature, followed by adding the compound of Formula (1), and keeping at a certain temperature for a period of time, then cooling to precipitate crystal, subsequently separating and drying the crystal to obtain the Crystal form A of the maleate of a compound of Formula (1), wherein the expression "a certain temperature" is preferably 40° C.-90° C., more preferably 50° C.-80° C.; the expression "a period of time" is preferably 20-90 min, more preferably 20-60 min, further preferably 20-40 min.

More preferably, the method for preparing the Crystal form A of the maleate of the compound of Formula (1) comprising:

adding maleic acid to an alcohol, a nitrile, a ketone, an ester, an oxygenated heterocycle, a halogenated hydrocarbon, an aromatic hydrocarbon, an alcohol/water, a ketone/water, a nitrile/water, an oxygenated heterocycle/water, an aprotic polar solvent/water, an aliphatic ether/an aprotic polar solvent or a halogenated hydrocarbon/an aprotic polar solvent, and heating to 40° C.-90° C., followed by adding the compound of Formula (1), and keeping the temperature at 40° C.-90° C. for 20-90 min, then cooling to precipitate crystal, subsequently separating and drying the crystal to obtain the Crystal form A of the maleate of the compound of Formula (1).

More preferably, the method for preparing the Crystal form A of the maleate of the compound of Formula (1) comprising:

adding maleic acid to ethanol, propanol, isopropanol, n-butanol, isobutanol, tert-butanol, acetonitrile, propionitrile, acetone, butanone, pentanone, methyl butyl ketone, methyl isobutyl ketone, methyl formate, ethyl formate, propyl formate, isopropyl formate, methyl acetate, ethyl acetate, propyl acetate, isopropyl acetate, methyl propionate, ethyl propionate, propyl propionate, isopropyl propionate, butyl acetate, isobutyl acetate, tetrahydrofuran, dihydropyran, tetrahydropyran, 1,4-dioxane, 1,2-dichloroethane, 1,1-dichloroethane, chloroform, toluene, xylene, ethanol/water, isopropanol/water, acetone/water, acetonitrile/water, 1,4-dioxane/water, dimethyl sulfoxide/water, N-methylpyrrolidone/water, N,N-dimethylformamide/water, methyl tert-butyl ether/N,N-dimethylformamide, methyl tert-butyl ether/N-methylpyrrolidone, chloroform/dimethyl sulfoxide, chloroform/N,N-dimethylformamide or chloroform/N-methylpyrrolidone, and heating to 50° C.-80° C., followed by adding the compound of Formula (1), and keeping the temperature at 50° C.-80° C. for 20-60 min, then cooling to precipitate crystal, subsequently separating and drying the crystal to obtain the Crystal form A of the maleate of the compound of Formula (1).

Further preferably, the method for preparing the Crystal form A of the maleate of the compound of Formula (1) comprising:

adding maleic acid to ethanol, isopropanol, acetonitrile, acetone, ethyl acetate, tetrahydrofuran, 1,4-dioxane, 1,2-dichloroethane, toluene, ethanol/water, isopropanol/water, acetone/water, acetonitrile/water, 1,4-dioxane/water, dimethyl sulfoxide/water, N-methylpyrrolidone/water, N,N-dimethylformamide/water, methyl tert-butyl ether/N,N-dimethylformamide, methyl tert-butyl ether/N-methylpyrrolidone, chloroform/dimethyl sulfoxide, chloroform/N,N-dimethylformamide or chloroform/N-methylpyrrolidone, and heating to 50° C.-80° C., followed by adding the compound of Formula (1), and keeping the temperature at 50° C.-80° C. for 20-60 min, then cooling to precipitate crystal, subsequently separating and drying the crystal to obtain the Crystal form A of the maleate of the compound of Formula (1).

Further more preferably, the method for preparing the Crystal form A of the maleate of the compound of Formula (1) comprising:

adding maleic acid to a mixed solvent of ethanol/water, isopropanol/water, acetone/water, acetonitrile/water, 1,4-dioxane/water, dimethyl sulfoxide/water, N-methylpyrrolidone/water, N,N-dimethylformamide/water, methyl tert-butyl ether/N,N-dimethylformamide, methyl tert-butyl ether/N-methylpyrrolidone, chloroform/dimethyl sulfoxide, chloroform/N,N-dimethylformamide or chloroform/N-methylpyrrolidone at a ratio of 1:30-30:1 by volume, and heating to 50° C.-80° C., followed by adding the compound of Formula (1), and keeping the temperature at 50° C.-80° C. for 20-60 min, then cooling to precipitate crystal, subsequently separating and drying the crystal to obtain the Crystal form A of the maleate of the compound of Formula (1).

In the above-mentioned methods, the drying may be carried out under reduced pressure or by ventilation, and the temperature for drying is no higher than 60° C., preferably 30° C.-55° C., more preferably 35° C.-50° C.; "cooling" in the expression "cooling to precipitate crystal" means decreasing the temperature to 10-30° C., preferably, the temperature is decreased by means of cooling in air, in oil bath, in water bath or in ice-water bath, more preferably the temperature is decreased by means of cooling in oil bath, that is, the solution is cooled with the cooling of the oil; the separation refers to separation by conventional methods such as filtration.

More preferably, adding the Crystal form A of the maleate of the compound of Formula (1) obtained by the above-mentioned methods to the single solvent or the mixed solvent, then sealing and stirring at a certain temperature for 60-90 h, preferably 70-80 h, followed by sucking filtrating to obtain the Crystal form A of the maleate of the compound of Formula (1), wherein, the certain temperature is preferably 40° C.-60° C., more preferably 50° C.

Generally, in order to analyze the obtained crystal, X-ray diffraction crystallography is applied.

When the crystal form of the present invention is determined by X-ray powder diffraction, on occasion, deviation of peaks between different measurements is observed due to the instrument or conditions, and the crystal, the spectral peaks of which fall into the deviation, is also covered in the scope of the crystal of the present invention. Therefore, when determining a crystal structure, the deviation shall be taken into account. Thus, when determining the degree of 2θ, a deviation of ±0.2° is employed by the applicant.

In the present invention, the pharmaceutical composition comprising the Crystal form A of the maleate of the compound of Formula (1) and one or more pharmaceutically acceptable carriers and/or diluents may be in any pharmaceutically acceptable dosage form, which is administered to a patient in need thereof orally, parenterally, rectally, or transpulmonarily. When administered orally, it can be prepared into a conventional solid formulation such as a tablet, a capsule, a pill, and a granule; it can also be prepared into an oral liquid formulation, such as an oral solution, an oral suspension, and a syrup. When preparing an oral formulation, suitable fillers, binders, disintegrating agents, lubricants, and the like may be added. When administered parenterally, it can be prepared into an injection, including a solution for injection, a sterile powder for injection and a concentrated solution for injection. The production of an injection can be carried out by conventional methods in the pharmaceutical field. When preparing an injection, no additives may be added, or suitable additives may be added depending on the nature of drugs. When administered rectally, it can be prepared into a suppository. When administered transpulmonarily, it can be prepared into an inhalant or a spraying agent, etc.

The pharmaceutical composition may further comprise a second therapeutic agent selected from an antitumor agent and/or an immunosuppressor, wherein the second therapeutic agent is selected from the group consisting of an antimetabolite, such as capecitabine, gemcitabine; a growth factor inhibitor, such as pazopanib, imatinib; an antibody, such as herceptin, bevacizumab; a mitotic inhibitor, such as paclitaxel, vinorelbine, docetaxel, doxorubicin; an antitumor hormone, such as letrozole, tamoxifen, fulvestrant; an alkylating agent, such as cyclophosphamide, carmustine; a metal platinum, such as carboplatin, cisplatin, oxaliplatin; a topoisomerase inhibitor, such as topotecan; and an immunosuppressor, such as everolimus.

In the present invention, the method for treating and/or preventing a hyperproliferative disease and a chronic obstructive pulmonary disease comprises administering to a patient in need of such a therapy an effective amount of the Crystal form A of the maleate of the compound of Formula (1), or in combination with the second therapeutic agent. The expression "in combination" includes simultaneously or subsequently.

In the present invention, the hyperproliferative disease is selected from the group consisting of a cancer and a non-cancerous disease; the cancer is selected from the group consisting of brain tumor, lung cancer, non-small cell lung cancer, squamous epithelial cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, esophageal adenocarcinoma, esophageal squamous cell carcinoma, solid tumor, non-Hodgkin's lymphoma, central nervous system tumor (neuroglioma, glioblastoma multiforme), prostate cancer and thyroid cancer; the noncancerous disease is benign hyperplasia of skin or prostate.

The Crystal form A of the maleate of the compound of Formula (1) of the present invention mainly has the following advantages of:

(1) simple and convenient preparation method, which is suitable for industrial production;

(2) good properties, facilitating detection, formulation, transportation and storage;

(3) high purity, low residual solvent content, high solubility, good stability and being easy to control quality;

(4) no or almost no hygroscopicity;

(5) excellent bioavailability; and (6) good anti-tumor effects and being useful for treating and/or preventing a hyperproliferative disease and a chronic obstructive pulmonary disease.

EXAMPLES

The above content of the present invention are further illustrated in detail by the following examples, but it should not be understood that the above subject matter of the present invention are just limited to the following examples. The techniques accomplished based on the above content of the present invention are all within the scope of the present invention.

The definitions represented by the following abbreviations are as follows:

DMSO: dimethyl sulfoxide

DMF: N,N-dimethylformamide

NMP: N-methylpyrrolidone

Example 1 Preparation I of Crystal Form a of the Maleate of the Compound of Formula (1)

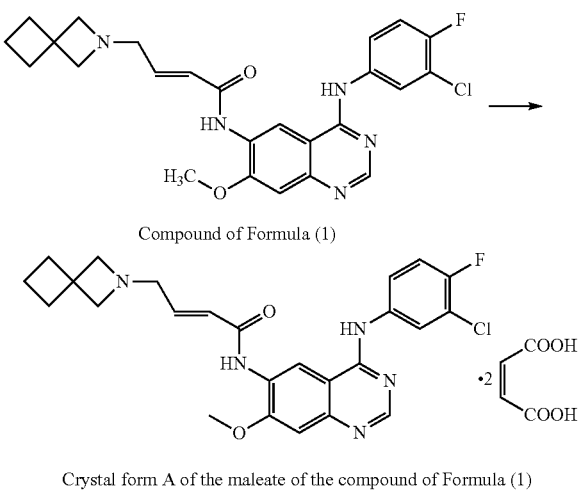

Compound of Formula (1)

Crystal form A of the maleate of the compound of Formula (1)

Maleic acid (241 mg) was placed in a 25 mL round-bottom flask, followed by the addition of ethanol (2.5 mL) and water (100 µL), the resultant mixture was heated to 75° C., and the compound of Formula (1) (500 mg) was added. Solids were precipitated out immediately after the mixture become clear. The system was maintained at 75° C. for 0.5 h, and then was slowly cooled to room temperature and filtered. The filter cake was washed with ethanol (2 mL) and dried. The resultant solid was measured by X-Ray Powder Diffraction (XRPD), Differential Scanning calorimetry (DSC), Thermogravimetric Analysis (TGA), Nuclear Magnetic Resonance (NMR) and High Performance Liquid Chromatography (HPLC).

X-Ray Powder Diffraction (XRPD)

Test conditions: the test was carried out in accordance with XRPD in Appendix IX F in Pharmacopoeia of the People's Republic of China (2010) Volume II. The details were as followed:

X-ray reflection parameter: Cu, Kα

Incident slit: 0.6 mm

Divergence slit: 1 mm

Scan mode: continuous

Scan range: 3.0-45.0 degrees

Sampling step size: 0.02 degrees

Scan time per step: 19.8 s

Detector angle: 2.0 degrees

The Measurement Result:

the XRPD pattern of the Crystal form A of the maleate of the compound of Formula (1) was shown in FIG. 1.

Differential Scanning Calorimetry (DSC)

The solid-state thermal properties of the Crystal form A of the maleate of the compound of Formula (1) were studied by DSC.

Test conditions: nitrogen purge was performed at 50 ml/min, data was collected at the heating rate of 10° C./min between 25° C. and 270° C., and plotting was performed with a downward endothermic peak.

Figure 2:
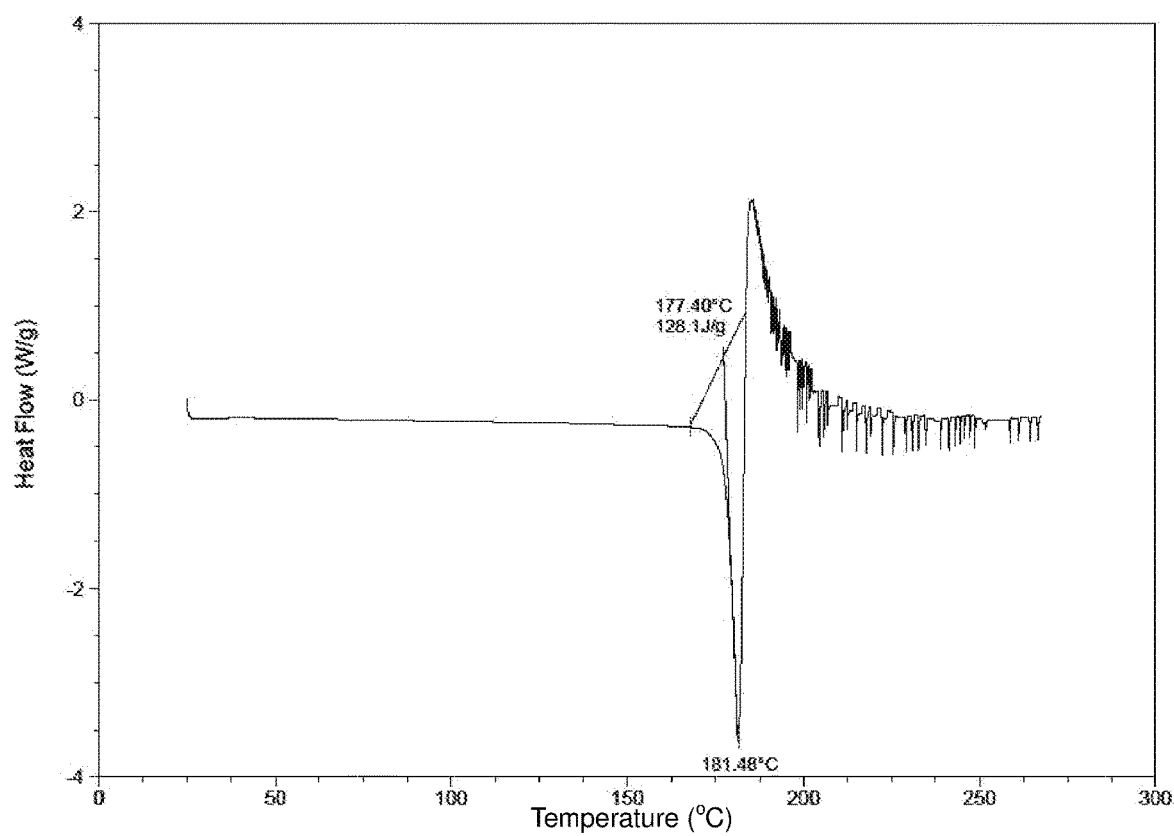
FIG. 2 shows the differential scanning calorimetry (DSC) thermogram of the Crystal form A of the maleate of a compound of Formula (1), wherein the ordinate represents heat flow (W/g), and the abscissa represents temperature (° C.).

Measurement result: the Crystal form A of the maleate of the compound of Formula (1) had an endothermic peak in the range from 170° C. to 185° C., and the DSC pattern was shown in FIG. 2.

In the DSC test, the measured starting temperature and maximum temperature were varied to a certain extent depending on the measurement parameters and heating rate.

Thermogravimetric Analysis (TGA)

Figure 3:
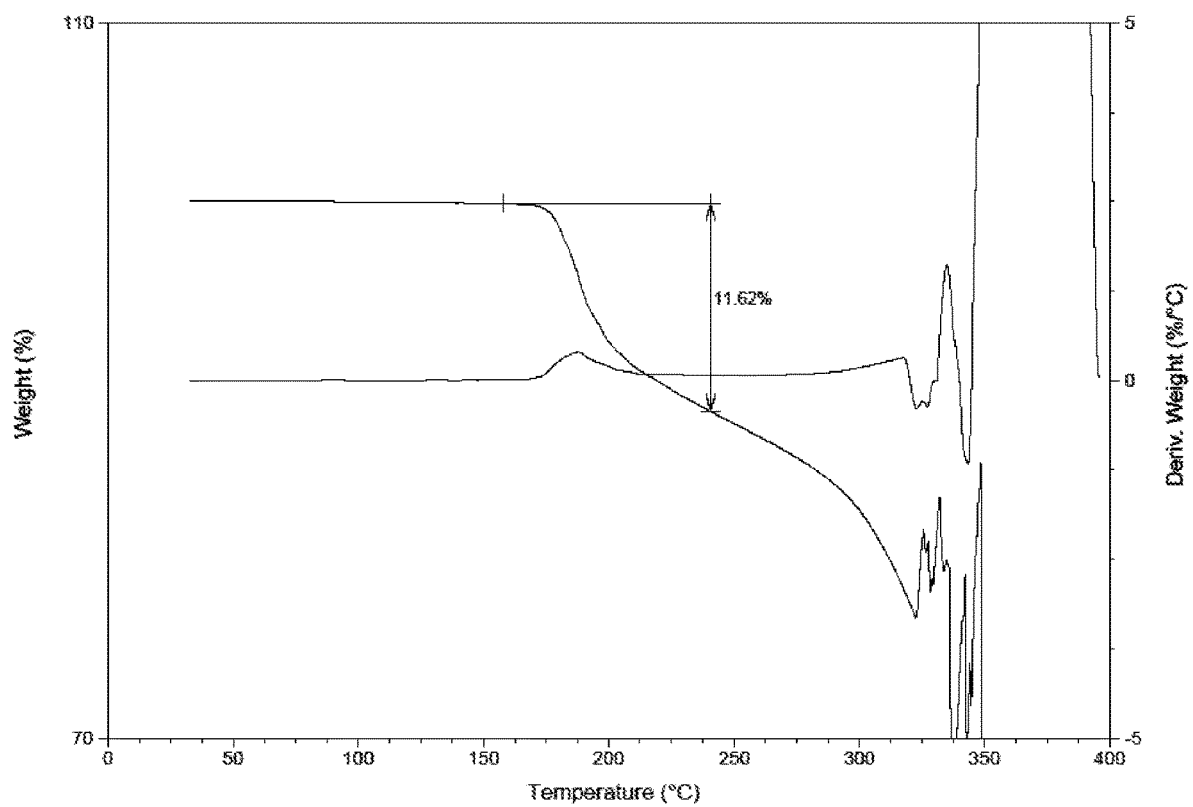
FIG. 3 shows the thermogravimetry (TG) thermogram and the derivative thermogravimetry (DTG) thermogram of the Crystal form A of the maleate of a compound of Formula (1), wherein the abscissa represents temperature (° C.), the left ordinate represents mass percent (%), and the right ordinate represents the relationship between weight-loss rate (%) and temperature.

Test conditions: nitrogen purge was performed at 60 ml/min, data was collected at a heating rate of 10° C./min between room temperature and 400° C., Measurement result: the Crystal form A of the maleate of the compound of Formula (1) had a weight loss of 11.62% in the range from 150° C. to 250° C., and its TG curve was shown in FIG. 3.

Nuclear Magnetic Resonance Analysis ($^1$H NMR)

Instrument: Bruker Advance III 400; Solvent: deuterated DMSO.

Figure 4:
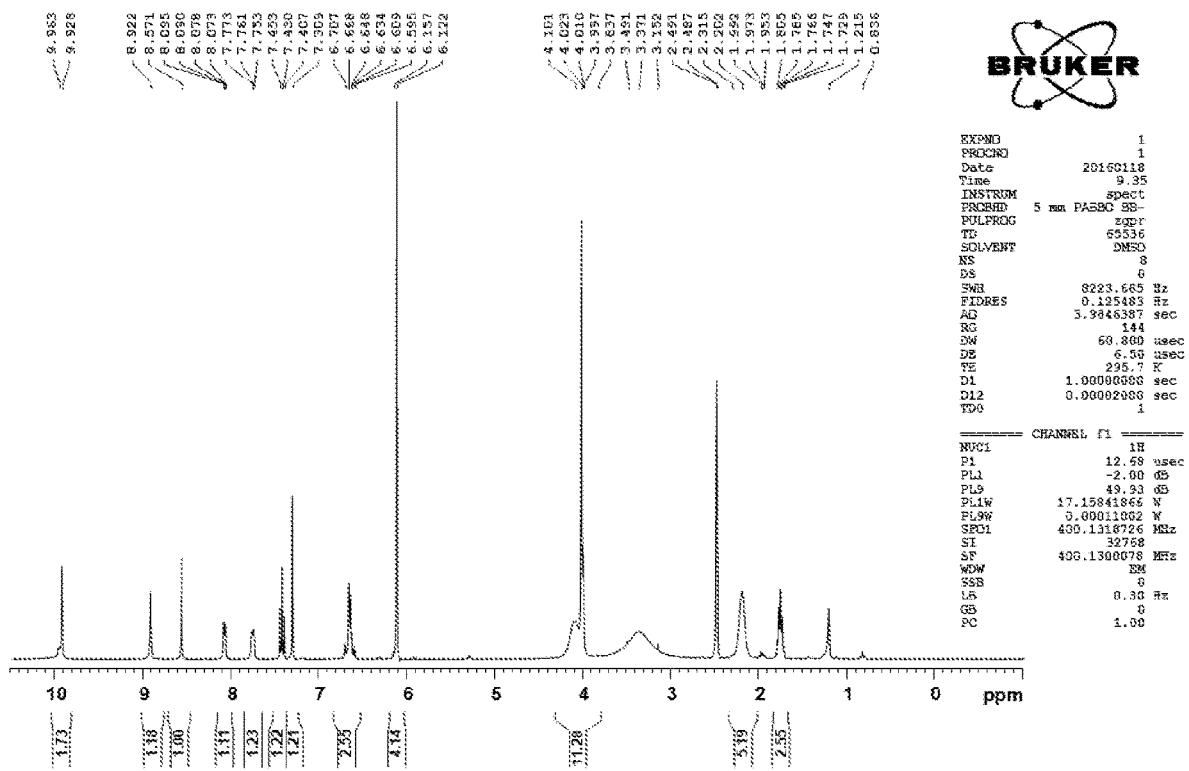
FIG. 4 shows the $^1$H NMR spectrum of the Crystal form A of the maleate of the compound of Formula (1).

Measurement result: the $^1$H NMR spectrum of the Crystal form A of the maleate of the compound of Formula (1) was shown in FIG. 4.

High Performance Liquid Chromatography (HPLC)

Measurement of maleic acid content: measurement was performed in accordance with High Performance Liquid Chromatography in General Rule 0512 of Pharmacopoeia of the People's Republic of China (2015) Volume IV.

Chromatographic conditions and system suitability test: the chromatographic column (HC-C8 250×4.6 mm, 5 μm) using octylsilane chemically bonded silica as a filler was applied, and the solution of 0.03 mol/L diammonium phosphate and 0.02 mol/L sodium perchlorate (diammonium phosphate (3.96 g) and sodium perchlorate (2.81 g) were dissolved in water (1000 ml), pH was adjusted to 4.0±0.1 with phosphoric acid)—methanol (95:5) was used as mobile phase; the detection wavelength was 214 nm; the column temperature was 30° C.; the flow rate was 0.5 ml/min. The reference substance maleic acid (12.5 mg) was accurately weighed, to which water was added to prepare the solution containing 0.06 mg maleic acid per 1 ml, as the reference solution; the reference solution (10 μl) was accurately measured, and injected into the liquid chromatographic instrument, and the chromatogram was recorded. The measurement was performed for 5 times in parallel, RSD % should not be greater than 2.0%, and the theoretical plate number should not be less than 3000 as calculated according to the maleic acid peak.

Measurement method: a suitable amount of the Crystal Form A of the maleate of the compound of Formula (1) was accurately weighed, and was dissolved and diluted by water, 2 samples as test solutions were prepared in parallel, the test solution (10 μl) was accurately measured, and injected into the liquid chromatographic instrument, and the chromatogram was recorded. The reference substance maleic acid was accurately weighed, 2 samples were prepared in parallel, and were determined by the same method; and the maleic acid content was calculated from the peak area according to the external standard method.

Measurement result: the maleic acid content was 32.0%-33.5%.

Example 2 Preparation II of the Crystal Form a of the Maleate of the Compound of Formula (1)

In a 10 mL single-neck round-bottom flask, the Crystal Form A of the maleate of the compound of Formula (1) (200 mg) prepared according to the method as described in Example 1 was added, followed by the addition of each solvent (2.0 mL) described in the following table, and the resultant mixture was sealed and heated to 50° C. After stirring for 72 h, suction filtration was performed, the resultant solid was subjected to XRPD test, DSC, TGA, and NMR analysis in the same manner as described in Example 1, and substantially the same spectra as those obtained in Example 1 were obtained.

| Solvent No. | Solvent type |
|---|---|
| 1 | acetone |
| 2 | acetone:water = 20:1 |
| 3 | acetonitrile |
| 4 | acetonitrile:water = 20:1 |
| 5 | 1,4-dioxane |
| 6 | 1,4-dioxane:water = 20:1 |
| 7 | ethanol |
| 8 | isopropanol |
| 9 | isopropanol:water = 20:1 |
| 10 | tetrahydrofuran |
| 11 | 1,2-dichloroethane |
| 12 | ethyl acetate |
| 13 | toluene |
| 14 | chloroform:DMSO = 20:1 |
| 15 | water:DMSO = 20:1 |
| 16 | DMF:methyl tert-butyl ether = 1:20 |
| 17 | DMF:chloroform = 1:20 |
| 18 | DMF:water = 1:20 |
| 19 | NMP:chloroform = 1:20 |
| 20 | NMP:methyl tert-butyl ether = 1:20 |
| 21 | NMP:water = 1:20 |

Example 3 Study on Stability of the Crystal Form a of the Maleate of the Compound of Formula (1)

Test Sample:

The Crystal form A of the maleate of the compound of Formula (1), prepared according to the method as described in Example 1.

The hydrochloride of the compound of Formula (1), prepared according to the preparation method as described in Example 2 in the specification of PCT/CN2012/000737.

Test Condition:

The Crystal form A of the maleate of the compound of Formula (1) and the hydrochloride of the compound of Formula (1) were kept at 70° C. for 3 d, and the samples were taken at Day 1 and Day 3, respectively, and were tested for purity and XRD, which were compared with those of the sample at Day 0.

The Crystal form A of the maleate of the compound of Formula (1) was kept under conditions of high moisture (25° C., RH92.5%) for 5 d, or under condition of light (4500LX±500LX) for 10 d, and was tested for purity and XRD, which were compared with those of the sample at Day 0.

Purity measurement: measurement was performed in accordance with High Performance Liquid Chromatography in Appendix II V D in Pharmacopoeia of the People's Republic of China (2010) Volume II.

XRD test: the same as described in Example 1.

Experimental Result

TABLE 1

Study result on stability

| Test sample | Experimental condition | Standing time | purity (%) | XRD |
|---|---|---|---|---|
| hydrochloride | 70° C. | 0 d | 98.4 | — |
| | | 1 d | 92.5 | — |
| | | 3 d | 89.0 | — |

TABLE 1-continued

Study result on stability

| Test sample | Experimental condition | Standing time | purity (%) | XRD |
|---|---|---|---|---|
| Crystal form A of the maleate | 70° C. | 0 d | 98.4 | as shown in FIG. 1 |
| | | 1 d | 98.0 | the same as the XRD pattern at Day 0 |
| | | 3 d | 97.4 | the same as the XRD pattern at Day 0 |
| Crystal form A of the maleate | 25° C., RH92.5% | 0 d | 98.6 | — |
| | | 5 d | 98.4 | — |
| Crystal form A of the maleate | 4500LX ± 500LX | 0 d | 98.6 | — |
| | | 10 d | 98.4 | the same as the XRD pattern at Day 0 |

Experimental Conclusion

No apparent change in purity of the Crystal form A of the maleate of the compound of Formula (1) was observed when was kept under the conditions of light (4500LX±500LX) for 10 d, high moisture (25° C., RH92.5%) for 5 d, or high temperature (70° C.) for 3 d. Whereas purity of the hydrochloride of the compound of Formula (1) decreased by 9.4% when was kept at high temperature (70° C.) for 3 d, indicating that the hydrochloride of the compound of Formula (1) is not stable at high temperature. As compared with the hydrochloride, the Crystal form A of the maleate shows good stability, which facilitates preparation, transportation and storage of drugs, and is even more beneficial to ensure the efficacy and safety of drug use.

Example 4 Study on Solubility of the Crystal Form a of the Maleate of the Compound of Formula (1)

1. Test Sample

The Crystal form A of the maleate of the compound of Formula (1), prepared according to the method as described in Example 1.

The hydrochloride of the compound of Formula (1), prepared according to the preparation method as described in Example 2 in the specification of PCT/CN2012/000737.

2. Measurement Method measurement was performed in accordance with High Performance Liquid Chromatography in Appendix II V D in Pharmacopoeia of the People's Republic of China (2010) Volume II.

3. Experimental Result

TABLE 2

| | Measurement result of solubility ($\mu$g/mL) | |
|---|---|---|
| pH of solution | Hydrochloride of the compound of Formula (1) | Crystal form A of the maleate of the compound of Formula (1) |
| $H_2O$ | 2200.6 | 4411.5 |
| 1.0 | 3255.8 | 20277.8 |
| 4.5 | 1883.0 | 9748.4 |
| 6.5 | 17.6 | 89.1 |
| 7.4 | 11.2 | 68.9 |

It can be seen from the experimental result above, as compared with the hydrochloride of the compound of Formula (1), the Crystal form A of the maleate had a higher solubility under various pH conditions, and showed apparent advantages.

Example 5 Study on Hygroscopicity of the Crystal Form a of the Maleate of the Compound of Formula (1)

1. Test Sample

The Crystal form A of the maleate of the compound of Formula (1), prepared according to the method described in Example 1.

The hydrochloride of the compound of Formula (1), prepared according to the preparation method as described in Example 2 in the specification of PCT/CN2012/000737.

2. Measurement Method measurement was performed in accordance with the Guidelines for pharmaceutical hygroscopicity test in General Rule 9103 of Pharmacopoeia of the People's Republic of China (2015) Volume IV.

3. Experimental Result

TABLE 3

| | Measurement result of hygroscopicity | |
|---|---|---|
| Test sample | Hygroscopic weight gain(%) | Hygroscopicity result |
| Hydrochloride of the compound of Formula (1) | 7.8 | hygroscopicity |
| Crystal form A of the maleate of the compound of Formula (1) | 0.07 | No or almost no hygroscopicity |

As seen from the experimental result above, the Crystal form A of the maleate of the compound of Formula (1) had a lower hygroscopicity than its hydrochloride.

What is claimed is:
1. Crystal form A of the maleate of the compound of Formula (1), (E)-N-(4-((3-chloro-4-fluorophenyl)amino)-7-methoxylquinazolin-6-yl)-4-(2-azaspiro[3.3]heptan-2-yl)-2-butenamide,

Formula (1)
wherein, the molar ratio of the compound of Formula (1) to maleic acid is 1:2,
wherein, the X-ray powder diffraction pattern of which has characteristic peaks at the 2θ positions of 5.2±0.2°, 10.3±0.2°, 11.3±0.2°, 13.8±0.2°, 16.2±0.2°, and 19.9±0.2°, as determined by using Cu-Kα radiation.

2. The Crystal form A of the maleate of the compound of Formula (1) according to claim 1, wherein, the DSC thermogram of which has an endothermic peak in the range from about 160° C. to 190° C.

3. The Crystal form A of the maleate of the compound of Formula (1) according to claim 1, which has a weight loss of about 5%-15% in the range from 150° C. to 250° C.

4. A method for preparing the Crystal form A of the maleate of the compound of Formula (1) according to claim 1, comprising reacting maleic acid with the compound of Formula (1) in a single solvent or a mixed solvent under heating, then cooling to precipitate crystal, followed by separating and drying to obtain the Crystal form A; wherein:
the single solvent is selected from the group consisting of ethanol, isopropanol, acetonitrile, acetone, ethyl acetate, tetrahydrofuran, 1,4-dioxane, 1,2-dichloroethane, and toluene; and
the mixed solvent is selected from the group consisting of ethanol/water, isopropanol/water, acetone/water, acetonitrile/water, 1,4-dioxane/water, dimethyl sulfoxide/water, N-methylpyrrolidone/water, N, N-dimethylformamide/water, methyl tert-butyl ether/N,N-dimethylformamide, methyl tert-butyl ether/N-methylpyrrolidone, chloroform/dimethyl sulfoxide, chloroform/N, N-dimethylformamide, and chloroform/N-methylpyrrolidone.

5. The method for preparing the Crystal form A of the maleate of the compound of Formula (1) according to claim 4, comprising: adding maleic acid to the single solvent or the mixed solvent, and heating to a certain temperature, followed by adding the compound of Formula (1), and keeping at a certain temperature for a period of time, then cooling to precipitate crystal, subsequently separating and drying the crystal to obtain the Crystal form A of the maleate of the compound of Formula (1), wherein the expression "a certain temperature" is 40° C.-90° C.; the expression "a period of time" is 20-90 min; in the expression "cooling to precipitate crystal", the "cooling" means decreasing the temperature to 10° C.-30° C.; the drying is conducted at no higher than 60° C.

6. The method for preparing the Crystal form A of the maleate of the compound of Formula (1) according to claim 4, further comprising recrystallizing the Crystal form A of the maleate of the compound of Formula (1) in a single solvent or a mixed solvent, wherein the single solvent and the mixed solvent are as defined in claim 4.

7. A pharmaceutical composition, comprising the Crystal form A of the maleate of the compound of Formula (1) according to claim 1 and one or more pharmaceutically acceptable carriers, optionally, further comprising one or more second therapeutic agents selected from an antitumor agent and/or an immunosuppressor, wherein the second therapeutic agent is selected from the group consisting of an antimetabolite, a growth factor inhibitor, an antibody, a mitotic inhibitor, an antitumor hormone, an alkylating agent, a metal platinum, a topoisomerase inhibitor, and an immunosuppressor.

8. The Crystal form A of the maleate of the compound of Formula (1) according to claim 1, the X-ray powder diffraction pattern of which also has characteristic peaks at the 2θ positions of 5.7±0.2°, 9.2±0.2°, 15.4±0.2°, and 18.7±0.2°.

9. The Crystal form A of the maleate of the compound of Formula (1) according to claim 1, the X-ray powder diffraction pattern of which also has characteristic peaks at the 2θ positions of 18.4±0.2°, 20.6±0.2°, 21.2±0.2°, 22.7±0.2°, and 23.6±0.2°.

10. The Crystal form A of the maleate of the compound of Formula (1) according to claim 1, the X-ray powder diffraction pattern of which also has characteristic peaks at the 2θ positions of 7.2±0.2°, and 24.6±0.2°.

11. The Crystal form A of the maleate of the compound of Formula (1) according to claim 1, the X-ray powder diffraction pattern is substantially as shown in FIG. 1.

12. The Crystal form A of the maleate of the compound of Formula (1) according to claim 1, the DSC thermogram of which has an endothermic peak in the range from 170° C. to 185° C.

13. The Crystal form A of the maleate of the compound of Formula (1) according to claim 1, the DSC thermogram of which is substantially as shown in FIG. 2.

14. The Crystal form A of the maleate of the compound of Formula (1) according to claim 1, which has a TGA thermogram substantially as shown in FIG. 3.

15. The pharmaceutical composition according to claim 7, wherein the second therapeutic agent is selected from the group consisting of capecitabine, gemcitabine, pazopanib, imatinib, herceptin, bevacizumab, paclitaxel, vinorelbine, docetaxel, doxorubicin, letrozole, tamoxifen, fulvestrant, cyclophosphamide, carmustine, carboplatin, cisplatin, oxaliplatin, topotecan, and everolimus.

* * * * *

UNITED STATES PATENT AND TRADEMARK OFFICE
CERTIFICATE OF CORRECTION

PATENT NO.         : 11,111,234 B2                                    Page 1 of 1
APPLICATION NO.    : 16/325051
DATED              : September 7, 2021
INVENTOR(S)        : J. Wang et al.

It is certified that error appears in the above-identified patent and that said Letters Patent is hereby corrected as shown below:

In the Claims

| Column | Line | |
|--------|------|---|
| 13     | 5    | change "20" to -- 2θ --. |

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*